(12) United States Patent
Mori et al.

(10) Patent No.: US 6,203,489 B1
(45) Date of Patent: Mar. 20, 2001

(54) FIBROUS PLUG FOR SUCKING TUBE

(75) Inventors: Hiroshi Mori; Hisashi Asoh, both of Tokyo (JP)

(73) Assignee: Fujihara Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/249,119

(22) Filed: Feb. 12, 1999

(30) Foreign Application Priority Data

Aug. 3, 1998 (JP) .................................................. 10-229964

(51) Int. Cl.$^7$ .............................. A61B 17/43; A61D 7/00
(52) U.S. Cl. .................................................................. 600/33
(58) Field of Search .............................. 600/33, 34, 35; 604/218, 906, 905, 412

(56) References Cited

U.S. PATENT DOCUMENTS 3,910,275 * 10/1975 Babey et al. ........................ 604/218

5,868,178 * 2/1999 Lecointe ............................. 604/412

* cited by examiner

*Primary Examiner*—Max Hindenburg
*Assistant Examiner*—Brian Szmal
(74) *Attorney, Agent, or Firm*—Arent Fox Kintner Plotkin & Khan

(57) ABSTRACT

A fibrous plug to be inserted in a sucking tube for use for collecting and preserving sperma, fertilized ovum or the like in artificial fertilization or transplantation for human and animals, composed of a gelatinizing material component present in a gas-permeable dispersed form and a supporting fiber component, wherein the gelatinizing material component is distributed finely among the supporting fiber component, so as to permit swelling of the gelatinizing material upon contact with a water-containing substance, such as sperma or the like, to build up an intrgrated water-tight sealing stopper together with the supporting fiber component.

12 Claims, 2 Drawing Sheets

FIBROUS PLUG FOR SUCKING TUBE

FIELD OF THE INVENTION

The present invention relates to a fibrous plug for a sucking tube for use in, for example, artificial fertilization or transplantation (of embrio or fertilized ovum) in human and animals, for sealing the tube after the tube is filled with a sperma or the like from a donor.

BACKGROUND OF THE INVENTION

In an artificial fertilization, sperma of a human or animal donor, which has been collected in a sucking tube made of a plastic material by sucking it thereinto, is discharged out via an open end thereof into the uterus of the female recipient by sliding a plug inserted in the sucking tube towards the open end thereof using a pushing element. In a transplantation of an embryo (fertilized ovum) also, similar procedures as above are pursued, while in this case the sperm is replaced by the embryo stored in a preserving liquor.

In the context of the specification of the present invention, "sperma or the like" is used to refer to sperma or transplantation liquor containing embryo(s), fertilized ovum(s), unfertilized ovum(s) and other cell(s).

In collecting a sperma or the like in a sucking tube, it is sucked into the tube from one end thereof by aspirating the tube internal air from the other end through a gas-permeable stopper made of, for example, sanitary cotton, stuffed in the tube, whereupon the stopper is removed from the sucking tube filled with the sperma or the like, whereupon the tube is sealed again by inserting therein a sterile non-permeable plug, in order to prepare for subsequent artificial fertilization.

For improving the actual procedures of such a laborious practice for collecting sperma or the like in the sucking tube, a technique was proposed meanwhile, in which a stopper composed of a first zone of gas-permeable cotton fibers, a second zone of gas permeable powdery gelatinizing material and a third zone of cotton fibers is stuffed in a sucking tube at one end portion thereof and the sperma or the like temporarily stored in a vessel is sucked up into the sucking tube via the other open end of the tube by aspirating out the internal air in the tube from the stopper-side open end of the tube through the gas-permeable stopper until the sperma or the like reaches the stopper, wherein the sperma or the like reacts with the powdery gelatinizing material to cause it to swell and gel to thereby fill up the tube as an integrated sealing stopper.

In the above technique, the gas-permeable stopper is composed of a powdery gelatinizing material sandwitched between two gas-permeable cotton fiber zones. When a sperma or the like is sucked into the sucking tube having such a stopper inserted therein, a part of the sperma or the like will pass through the inside cotton zone and reach the powdery gelatinizing material. Upon contact of the powdery gelatinizing material with the spema or the like, the gelatinizing material swells by absorbing water from the sperma or the like to fill up the tube and, then, it reaches gellation, while binding with a part of the cotton fibers to build up an integrated sealing stopper. Then, the open end of the sucking tube through which the sperma or the like is sucked thereinto is sealed by welding by an appropriate method, such as an ultrasonic heat treatment, in order to preserve the so-collected sperma or the like therein until it is transferred to the recipient.

However, this technique requires, at least with respect to the preparation of the three-zone stopper in a portion of one end of the sucking tube, three working steps for inserting the first zone of cotton fibers, the second zone of powdery gelatinizing material and the third zone of cotton fiber each in a separate procedure into a thin sucking tube having a inner diameter of, usually, 2.6 mm or 1.55 mm. For such insertion works, a plurality of specifically devised precise instruments are necessary.

This technique is also disadvantageous in that the gelatinizing material is present as a powder and is not only difficult to weigh it minutely but also apt to be scattered around upon its insertion into the tube to thereby pollute the product and assembly and, in some cases, the powder may even be scattered beyond the cotton zone to the collecting space for the sperma or the like and may damage the live activity of the spermatozoon or the embedding rate of fertilized ovum.

In the context of the specification of the present invention, the "gelatinizing material" is used to refer to a material which will swell upon contact with a water-containing liquid, such as sperma or the like, by absorbing water therefrom and reach eventually gellation to build up an integrated sealing stopper together with the supporting fibers. Concrete examples therefor include polyvinyl alcohol, dextrin, casein and the like.

SUMMARY OF THE INVENTION

An object of the present invention is to provide, in view of the above circumstances, a fibrous plug to be inserted in a sucking tube allowing simplified practices for collecting sperma or the like in the tube and for performing artificial fertilization or transplantation using low cost instruments therefor.

Another object of the present invention is to provide a method for the use of a sucking tube having such a fibrous plug inserted therein for artificial fertilization or transplantation of embryo in human or animal.

The above objects are achieved according to the present invention by a fibrous plug and a method as defined below:

(1) A fibrous plug to be inserted in a sucking tube, comprising fibers of a gelatinizing material and supporting fibers, wherein the gelatinizing material fibers are distributed finely among the supporting fibers.

(2) A method for the use of a sucking tube having the fibrous plug as defined in above (1) for artificial fertilization or transplantation of embryo in human or animal, comprising aspirating out the internal air of the sucking tube via an end thereof through the fibrous plug to suck a sperma or the like from the donor into the tube via the other end of the sucking tube cut open directly before the use, so as the sperma or the like to reach the plug and to build up a sealing stopper, whereupon the open end via which the sperma or the like is sucked into the tube is sealed for preserving the sperma or the like therein till the sucked-in sperma or the like is transferred therefrom in a conventional way to the recipient.

DETAILED DESCRIPTION OF THE INVENTION

Figure 1:
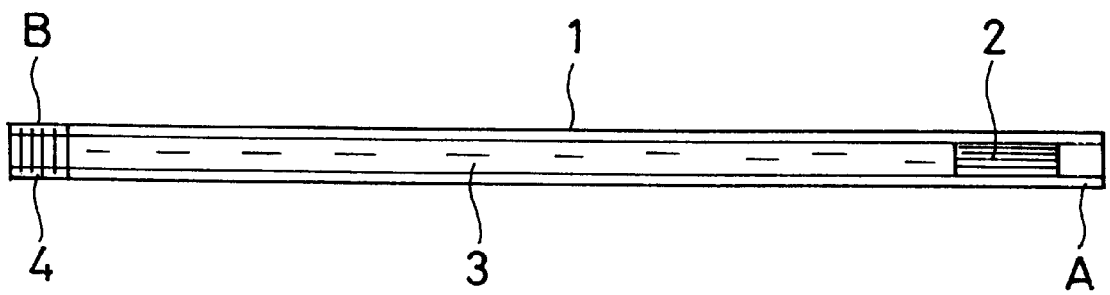
FIG. 1 shows a sucking tube provided therein with the fibrous plug according to the present invention in a schematic explanatory sectional view.

The sucking tube in which the fibrous plug according to the present invention is inserted may favorably be made of an appropriate resilient polymeric material, wherein special preference is given to that made of a biodegradable plastic material. Such a sucking tube is used in artificial fertilization and in transplantation in human and animals, especially livestocks. In artificial fertilization, sperma from a donor of human or animal stored temporarily in a vessel under dilution with preserving liquor is sucked into the sucking tube by aspirating out the internal air of the sucking tube via an open end thereof through the gas-permeable fibrous plug inserted therein near this opening.

Animals include livestocks, such as bovine, swine, sheep, goat and chicken, and others including pet animals.

The fibrous plug according to the present invention is used in the place of the previously proposed combined stopper composed of a cotton fiber zone, a powdery gelatinizing material zone and a further cotton fiber zone mentioned above. The fibrous plug according to the present invention comprises supporting fibers and, uniformly distributed among them, a finely scattered gelatinizing material, existing in a mixed state for allowing building up of an integrated sealing stopper when the gelatinizing material contained therein becomes swollen and gelled by absorbing water upon contact with a water-containing substance, such as a sperma or an ovum-containing liquor. The two essential components, namely, the gelatinizing material and the supporting fiber, may be present in the fibrous plug according to the present invention in any voluntary mixture, so long as they build up, upon contact with a water-containing liquid, an integrated sealing stopper by swelling and gellation of the gelatinizing material.

THE BEST MODE FOR EMBODYING THE INVENTION

In an emboiment, the fibrous plug according to the present invention may be in a form of simple fiber mixture composed of fibers of the gelatinizing material and the supporting fibers.

Thus, the gelatinizing material may be present in the fibrous plug either in a form of fiber, which is in combination with the supporting fiber as a simple fiber mixture, as a woven fabric, as a non-woven fabric or as a braided cord, in a form of coating film, which is coated over each of the supporting fibers, or in a form of a binder which binds the supporting fibers with each other.

The fiber of gelatinizing material is prepared by filamenting or spinning from a solution of a gelatinizing material, such as polyvinyl alcohol or so on, in water or in an adequate solvent and drying the resulting fiber. The resulting gelatinizing material fiber has a solubilization temperature in water of, preferably, 3–8° C. and can swell and gel upon contact with a water-containing substance, such as sperma or the like.

The supporting fiber may consist of a natural fiber, such as cotton, hemp, silk and wool, a synthetic fiber or an inorganic fiber as well as a mixture or a mixed spun yarn of them.

The gelatinizing material fiber and the supporting fiber may preferably be used as a mixed yarn. Many such mixed yarns may be bundled into a sliver, which can be inserted in the sucking tube as the fibrous gas-permeable plug according to the present invention. While the proportion of fibers of the gelatinizing material to the supporting fibers in the fibrous plug according to the present invention is not specifically restricted, it may preferably range from 2:1 to 1:1 in terms of the ratio of their sectional areas in the sliver. If, however, the proportion of fibers of the gelatinizing material in the sliver is chosen at too high a value, the resulting fibrous plug will exhibit a lower stiffness, so that a difficulty may be brought about in the injection of the sperma or the like collected in the sucking tube into the uterus of the recipient. On the other hand, when the proportion of fibers of the gelatinizing material in the sliver is too low, no complete swelling and gellation upon contact with sperma or the like would be assured.

In an alternative embodiment of the present invention, supporting fibers coated each with a layer of a gelatinizing material may be employed for preparing the fibrous gas-permeable plug according to the present invention. When the so-prepared fibrous plug according to the present invention is brought into contact with a water-containing substance, such as sperma or the like, the coated layer of the gelatinizing material will swell and fill up the suckuing tube as an integrated sealing stopper together with the supporting fiber.

In a further alternative embodiment of the fibrous plug according to the present invention, the plug may be composed of a mass of the supporting fibers in which the fibers are bound with each other by the gelatinizing material served as a binder distributed among the mass of the fibers. This fibrous plug may be prepared by distributing fine droplets or particles of a wetted or liquid form gelatinizing material among a mass of the supporing fibers, drying the resulting mass and forming the so-dried mass into the fibrous plug.

In using the fibrous plug according to the present invention inserted in a resilient sucking tube for artificial fertilization, sperma from a donor of human or animal stored temporarily in a vessel under dilution with a preserving liquor is sucked into the sucking tube until it reaches the fibrous plug by aspirating out the internal air of the sucking tube via an open end thereof on the side of the inserted gas-permeable fibrous plug therethrough, whereupon the other open end of the tube through which the sperma is sucked thereinto is sealed by welding by, for example, ultrasonic heat treatment, for preserving the sperma until it is transferred to the recipient. On transferring the sperma collected in the sucking tube to the recipient, the weld-sealed end of the sucking tube is cut open and is inserted into the uterus of the recipient, whereupon the fibrous plug, which has been swollen and now been converted into an integrated sealing stopper, is pushed slidingly within the tube towards the cut open end by an adequate pusher, in order to inject the sperma thereinto.

As described above, the fibrous plug according to the present invention to be inserted in sucking tube for use in artificial fertilization or transplantation consists in a combination of a gelatinizing material component present in a gas-permeable dispersed form and a gas-permeable supporting fiber component and, thus, permits easy installation in the sucking tube while guaranteeing enough gas-permeability before the sperma or the like sucked into the tube reaches the fibrous plug and causes swelling of the plug into an integrated water-tight sealing stopper, whereby easy and smooth works of collection of the sperma or the like and of transferrence thereof to the recipient are permitted.

EXAMPLE

Below, the present invention will be described by way of Examples.

Example 1

As shown in FIG. 1, a sucking tube 1 provided therein with a fibrous plug 2 according to the present invention has, collected therein, a sperma 3 from a livestock, of which open end B has been sealed (4) by welding by heat-pressing.

Figure 2:
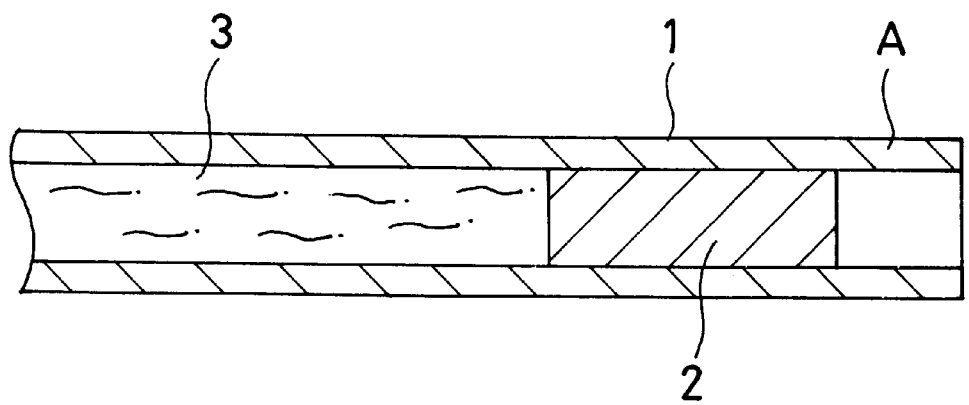
FIG. 2 is a partial enlagement of the sucking tube shown in FIG. 1.

In FIG. 2, a part of the sucking tube of FIG. 1 is shown in an enlarged sectional view. The fibrous plug 2 consists of a fiber mixture composed of mixed-spun yarns from the gelatinizing material fiber 5 made of a gelled polyvinyl alcohol and the supporting fiber 6. The gelatinizing material fiber 5 has been swollen by absorbing water from the sperma 3 and has built up together with the supporting fiber 6 an integrated water-tight sealing stopper.

Example 2

Figure 3:
FIG. 3 illustrates a typical state of mixed braiding of the fibers of gelatinizing material with the supporting fibers in cross sectional view.
Figure 4:
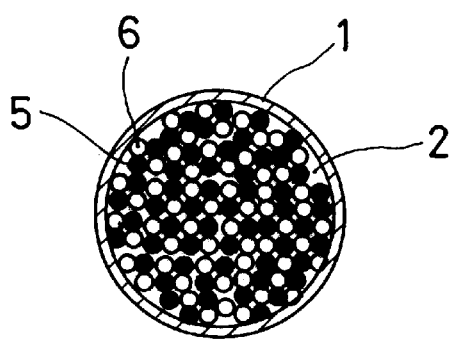
FIG. 4 illustrates a typical braided cord according to the present invention in a schematic sectional view.

Here, the sucking tube 1 is provided therein with a fibrous plug according to the present invention prepared from, as shown schematically in FIGS. 3 and 4, a bundled sliver constituted of mixed spun yarns each made of two filaments 5 of gelatinizing material and two supporting filaments 6.

Example 3

Figure 5:
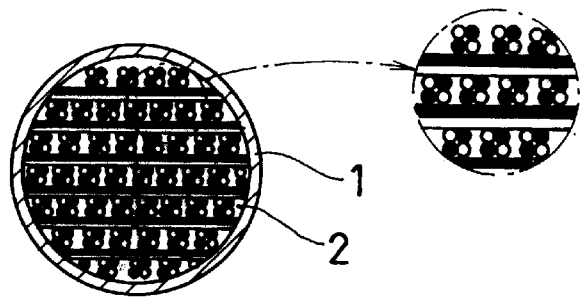
FIG. 5 illustrates an embodiment of the fibrous plug according to the present invention in a form of woven fabric in a schematic sectional view.

Here, the sucking tube 1 is provided therein with a fibrous plug according to the present invention constituted of, as shown schematically FIG. 5, a woven fabric woven from a mixed-spun yarn of gelatinizing material fiber 5 and supporting fiber 6.

Example 4

Figure 6:
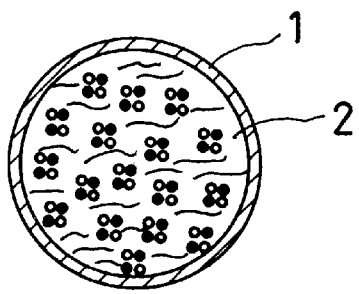
FIG. 6 illustrates an embodiment of the fibrous plug according to the present invention in a form of non-woven fabric in a schematic sectional view.

The sucking tube 1 is provided therein with a fibrous plug prepared from, as shown schematically in FIG. 6, a non-woven fabric composed of fibers 5 of the gelatinizing material and the supporting fibers 6.

As described above, procedures for artificial fertilization and transplantation can be performed easily in a simple manner using the fibrous plug according to the present invention, since the fibrous plug according to the present invention is a single compact piece made from composite fiber composed of a gelatinizing material component and a support fiber component. The fibrous plug according to the present invention permits a quantitative use, since the proportion of the gelatinizing material component and the supporting fiber component is always constant due to the use of a predetermined proportion of the components for the preparation of the plug. When biodegradable substances are employed for the sucking tube as well as for the fibrous plug, an environment-tendering product can be provided.

What is claimed is:

1. A fibrous plug to be inserted in a sucking tube, comprising fibers of a gelatinizing material and supporting fibers, wherein the gelatinizing material fibers are distributed finely among the supporting fibers.

2. A fibrous plug as claimed in claim 1, wherein the plug is made of a woven fabric.

3. A fibrous plug as claimed in claim 1, wherein the plug is made of a non-woven fabric.

4. A fibrous plug as claimed in claim 1, wherein the plug is made of a braided cord.

5. A method for the use of a sucking tube having the fibrous plug as claimed in claim 1 inserted therein for artificial fertilization or transplantation of embryo in human or animal, comprising aspirating out the internal air of the sucking tube via an end thereof through the fibrous plug to suck a sperma from the donor into the tube via the other end of the sucking tube cut open directly before the use, so as the sperma to reach the plug and to build up a sealing stopper, whereupon the open end from which the sperma is sucked into the tube is sealed for preserving the sperma therein till the sucked-in sperma or the like is transferred therefrom in a conventional way to the recipient.

6. A method for the use of a sucking tube having the fibrous plug as claimed in claim 2 inserted therein for artificial fertilization or transplantation of embryo in human or animal, comprising aspirating out the internal air of the sucking tube via an end thereof through the fibrous plug to suck a sperma from the donor into the tube via the other end of the sucking tube cut open directly before the use, so as the sperma to reach the plug and to build up a sealing stopper, whereupon the open end from which the sperma is sucked into the tube is sealed for preserving the sperma or the like therein till the sucked-in sperma is transferred therefrom in a conventional way to the recipient.

7. A method for the use of a sucking tube having the fibrous plug as claimed in claim 3 inserted therein for artificial fertilization or transplantation of embryo in human or animal, comprising aspirating out the internal air of the sucking tube via an end thereof through the fibrous plug to suck a sperma from the donor into the tube via the other end of the sucking tube cut open directly before the use, so as the sperma to reach the plug and to build up a sealing stopper, whereupon the open end from which the sperma or the like is sucked into the tube is sealed for preserving the sperma therein till the sucked-in sperma is transferred therefrom in a conventional way to the recipient.

8. A method for the use of a sucking tube having the fibrous plug as claimed in claim 4 inserted therein for artificial fertilization or transplantation of embryo in human or animal, comprising aspirating out the internal air of the sucking tube via an end thereof through the fibrous plug to suck a sperma from the donor into the tube via the other end of the sucking tube cut open directly before the use, so as the sperma to reach the plug and to build up a sealing stopper, whereupon the open end from which the sperma or the like is sucked into the tube is sealed for preserving the sperma therein till the sucked-in sperma is transferred therefrom in a conventional way to the recipient.

9. A fibrous plug to be inserted in a sucking tube, comprising fibers of a supporting material each coated with a layer of a gelatinizing material.

10. A method for the use of a sucking tube having the fibrous plug as claimed in claim 9 inserted therein for artificial fertilization or transplantation of embryo in human or animal, comprising aspirating out the internal air of the sucking tube via an end thereof through the fibrous plug to suck a sperma from the donor into the tube via the other end of the sucking tube cut open directly before the use, so as the sperma to reach the plug and to build up a sealing stopper, whereupon the open end from which the sperma is sucked into the tube is sealed for preserving the sperma or the like therein till the sucked-in sperma is transferred therefrom in a conventional way to the recipient.

11. A fibrous plug to be inserted in a sucking tube, comprising supporting fibers bound with each other by a gelatinizing material, prepared by dispersing the gelatinizing material in a liquid form among heaped mass of the supporting fibers and, then, solidifying the gelatinizing material.

12. A method for the use of a sucking tube having the fibrous plug as claimed in claim 11 inserted therein for artificial fertilization or transplantation of embryo in human or animal, comprising aspirating out the internal air of the sucking tube via an end thereof through the fibrous plug to suck a sperma from the donor into the tube via the other end of the sucking tube cut open directly before the use, so as the sperma to reach the plug and to build up a sealing stopper, whereupon the open end from which the sperma is sucked into the tube is sealed for preserving the sperma therein till the sucked-in sperma is transferred therefrom in a conventional way to the recipient.

* * * * *